(12) United States Patent
Harris

(10) Patent No.: US 11,951,031 B2
(45) Date of Patent: Apr. 9, 2024

(54) ANTI-SNORING MOUTH GUARD

(71) Applicant: Chad Harris, Du Quoin, IL (US)

(72) Inventor: Chad Harris, Du Quoin, IL (US)

( * ) Notice: Subject to any disclaimer, the term of this patent is extended or adjusted under 35 U.S.C. 154(b) by 0 days.

(21) Appl. No.: 17/862,512

(22) Filed: Jul. 12, 2022

(65) Prior Publication Data

US 2023/0011147 A1  Jan. 12, 2023

Related U.S. Application Data

(60) Provisional application No. 63/220,833, filed on Jul. 12, 2021.

(51) Int. Cl.
*A61F 5/56* (2006.01)

(52) U.S. Cl.
CPC .................................... *A61F 5/566* (2013.01)

(58) Field of Classification Search
CPC ...... A61F 2005/563; A61F 5/56; A61F 5/566; A61C 7/08; A61C 7/36; A63B 71/085; A63B 2071/086; A63B 2071/088
See application file for complete search history.

(56) References Cited

U.S. PATENT DOCUMENTS

| | | | | |
|---|---|---|---|---|
| 3,132,647 A | * | 5/1964 | Corniello | A61F 5/566 D24/176 |
| 3,207,153 A | * | 9/1965 | Goldstein | A63B 71/085 D24/176 |
| 5,556,357 A | * | 9/1996 | Hanna | A63B 23/032 601/39 |
| 5,607,300 A | * | 3/1997 | Tepper | A61C 7/00 433/24 |
| 6,766,802 B1 | * | 7/2004 | Keropian | A61F 5/566 128/859 |
| 8,127,769 B2 | * | 3/2012 | Walker | A61F 5/566 433/140 |
| 8,333,202 B2 | * | 12/2012 | Lyons | A61M 16/0495 433/7 |
| 8,881,733 B1 | * | 11/2014 | Harkins | A61C 7/08 128/860 |
| 9,937,019 B1 | * | 4/2018 | Copps | A61C 19/06 |
| 10,383,758 B1 | * | 8/2019 | Greenburg | A61F 5/566 |
| 10,772,756 B2 | * | 9/2020 | Vaska | A61F 5/566 |
| 10,772,757 B1 | * | 9/2020 | Harris | A61F 5/56 |
| 11,033,421 B1 | * | 6/2021 | Davis | A61F 5/566 |

(Continued)

*Primary Examiner* — Camtu T Nguyen
(74) *Attorney, Agent, or Firm* — Dale J. Ream

(57) ABSTRACT

An anti-snoring mouth guard for insertion into a mouth of a user for decreasing snoring and the effects of sleep apnea includes a mouthpiece portion having a bottom wall and a pair of upstanding side walls displaced and opposite one another and extending upwardly from the bottom wall, said mouthpiece having a hemispherical configuration that is complementary to a shape of the user's teeth. Collectively, the bottom wall and pair of side walls define a channel operable to receive teeth of a user's upper pallet. The anti-snoring mouth guard includes tongue depressor portion having a proximal end coupled to the mouthpiece and having a body extending rearwardly at a generally downward angle. A brace may extend between rear ends of the mouthpiece portion and define levels by which the tongue depressor may be inserted such that the tongue depressor may be adjusted vertically and front-to-back.

2 Claims, 4 Drawing Sheets

(56) References Cited

U.S. PATENT DOCUMENTS

| | | | |
|---|---|---|---|
| 2008/0041396 A1* | 2/2008 | Lucker | A61F 5/566 128/845 |
| 2008/0210244 A1* | 9/2008 | Keropian | A61F 5/566 128/848 |
| 2011/0297162 A1* | 12/2011 | Navarro Segura | A61F 5/566 128/848 |
| 2013/0125902 A1* | 5/2013 | Danielian | A61B 17/24 128/859 |

* cited by examiner

ANTI-SNORING MOUTH GUARD

REFERENCE TO RELATED APPLICATIONS

This application claims the priority benefit of provisional patent application Ser. No. 63/220,833 filed Jul. 12, 2021, titled ANTI-SNORING MOUTH GUARD which is incorporated in its entirety herein by reference. This application is related to non-provisional patent application Ser. No. 16/678,422 filed Nov. 8, 2019 titled ANTI-SNORING MOUTH GUARD, now U.S. Pat. No. 10,772,757, which claims the priority benefit of provisional patent application Ser. No. 62/862,912 filed Jun. 18, 2019, titled ANTI-SNORING MOUTH GUARD.

BACKGROUND OF THE INVENTION

This invention relates generally to anti-snoring devices and, more particularly, to a mouthpiece for insertion into a person's mouth having a tongue depressor that suppresses or prevents the person's tongue from impeding his airway and, as a result, reducing or eliminating snoring and obstructive apnea.

Snoring is often perceived merely as "noisy breathing" when sleeping. Snoring happens when you can't move air freely through your nose and throat during sleep. However, snoring may actually be much more of a health concern, such as heart disease or another breathing dysfunction. About one-half of people who snore loudly have obstructive sleep apnea. Sleep apnea is a potentially serious sleep disorder in which breathing repeatedly stops and starts. Persons with sleep apnea often wear a CPAP mask for years to prevent the negative effects of sleep apnea, including possible death. Prevention of obstructive snoring, then, is of prime interest to persons with dangerous snoring and sleep apnea.

Various devices have been proposed for decreasing or preventing snoring. Although presumably effective for their intended purposes, there is still a need for a lightweight and simple solution for preventing a person's tongue from obstructing the person's airway and allowing snoring to occur.

Therefore, it would be desirable to have a mouth guard for insertion into a mouth of a user for decreasing snoring and the effects of sleep apnea. Further, it would be desirable to have a mouth guard for insertion into a mouth of a snorer having a tongue depressor portion that is adjustable vertically, longitudinally, and angularly.

SUMMARY OF THE INVENTION

An anti-snoring mouth guard for insertion into a mouth of a user for decreasing snoring and the effects of sleep apnea according to the present invention includes a mouthpiece portion having a bottom wall and a pair of upstanding side walls displaced and opposite one another and extending upwardly from the bottom wall, the mouthpiece having a hemispherical configuration that is complementary to a shape of the user's teeth. Collectively, the bottom wall and pair of side walls define a channel operable to receive teeth of a user's upper pallet. The anti-snoring mouth guard includes a proximal end coupled to the mouthpiece and having a body extending rearwardly at a generally downward angle. The tongue depressor portion may include adjustment structures so as to adjustable vertically, front-to-back, presumably by a dentist or dental technician.

Therefore, a general object of this invention is to provide a mouth guard receivable on the upper pallet of a user's teeth and operable to hold a user's tongue so as to decrease snoring and the affects of sleep apnea.

Another object of this invention is to provide a mouth guard, as aforesaid, in which a tongue depressor portion is vertically adjustable relative to the mouthpiece portion.

Still another object of this invention is to provide a mouth guard, as aforesaid, in which a tongue depressor portion is longitudinally (frontwardly and rearwardly) adjustable relative to the mouthpiece portion.

Yet another object of this invention is to provide a mouth guard, as aforesaid, that can inhibit or stop snoring with a mouthpiece for only the upper pallet of a person's mouth.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1b is exploded view of the anti-snoring mouth guard as in FIG. 1a;

FIG. 2a is a top view of the anti-snoring mouth guard as in FIG. 1a;

FIG. 2b is a sectional view taken along line 2b-2b of FIG. 2a;

FIG. 3b is an exploded view of the anti-snoring mouth guard as in FIG. 3a;

FIG. 4a is a top view of the anti-snoring mouth guard as in FIG. 3a;

FIG. 4b is a sectional view taken along line 4b-4b of FIG. 4a; and

DESCRIPTION OF THE PREFERRED EMBODIMENT

Figure 1A:
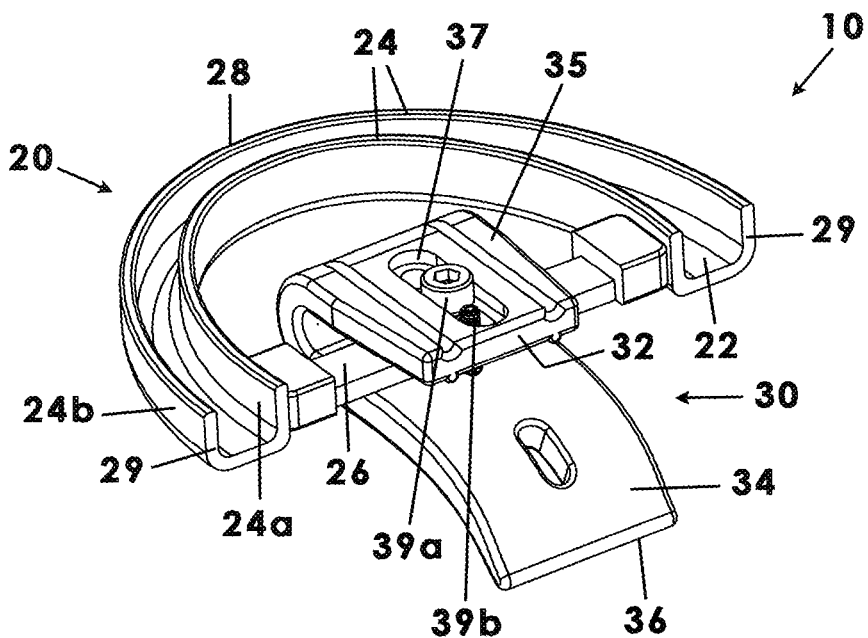
FIG. 1a is a perspective view of an anti-snoring mouth guard according to an embodiment of the present invention.

An anti-snoring mouth guard according to a preferred embodiment of the present invention will now be described with reference to FIGS. 1a to 4c of the accompanying drawings. The anti-snoring mouth guard 10 may include a mouthpiece portion 20 and tongue depressor portion 30 coupled to the mouthpiece.

With regard to FIG. 1a to 3b, the mouthpiece portion 20 of the anti-snoring mouth guard 10 may include a bottom wall 22 and a pair of upstanding side walls 24 extending upwardly from the bottom wall 22. The side walls 24 are displaced from one another and are parallel to one another. Collectively, the bottom wall 22 and pair of side walls 24 define an interior area, such as a channel or trough operable to selectively receive the teeth of a person's upper pallet. In other words, the mouthpiece portion 20 has a generally hemispherical configuration complementary to a user's upper teeth and can be inserted comfortably into a user's mouth, such as at night. It is understood that the side walls 24 include an inner side wall 24a and an outer side wall 24b, each having interior surfaces facing one another that may be contoured or define recesses operable to receive associated teeth in nested relationships, respectively. The front or apex of the mouthpiece portion 20 may be referred to as a front section 28. By contrast, the pair of side walls 24 extends away from the apex rearwardly to terminal ends, respectively, and which will be referred to as rear ends 29 of the mouthpiece 20. As shown, the rear ends 29 have an open configuration as the exact number and size of a patient's teeth will not be known at a point of manufacturing.

The mouthpiece portion 20 includes a support bridge 26 adjacent at least one rear end 29 of the mouthpiece. In an embodiment, the support bridge 26 may be positioned along an inner surface of the inner side wall 24a of the pair of side walls and will be discussed in more detail later. Preferably, however, the support bridge 26 extends between respective rear ends 29 of the pair of side walls (or, more particularly, from rear ends of the inner side wall 24a) and may be referred to as a brace—also using reference numeral 26.

Further, the tongue depressor portion 30 of the anti-snoring tongue guard 10 includes a proximal end 32 coupled to the bridge 26 of the mouthpiece portion 20 and includes a body 34 extending from the proximal end 32. Preferably, the proximal end 32 is coupled to the mouthpiece side of the bridge 26 and the body 34 curves around (i.e., under) the bridge 26 such that the proximal end 32 and body 34 may have a generally U-shaped configuration such that the proximal end 32 is parallel to at least a portion of the body 34. The proximal end 32 of the body 34 of the tongue depressor portion 30 may have a width that is the same or complementary to the distance between interior surfaces of respective interior side walls of the mouthpiece. In other words, the proximal end 32 of the tongue depressor portion 30 may extend completely between peripheral walls of the mouthpiece portion 20. However, in some embodiments, the proximal end 32 may have a decreased width not extending completely between peripheral walls of the mouthpiece portion 20. The body 34 of the tongue depressor portion 30 extends rearwardly from the proximal end 32 at a generally downward angle so as to bear against a user's tongue when the mouthpiece portion 20 is inserted into the user's mouth. The tongue depressor portion 30 may include a distal end 36 opposite the proximal end 32 and extending away from the body 34. In an embodiment, the body 34 may have a curved, wavy, or irregular configuration, particularly proximate the distal end 36.

In another critical aspect, the tongue depressor portion 30 may be movable front-to-rear (longitudinally) and also upwardly-downwardly (e.g., vertically) relative to the mouthpiece portion 20, as will be described below and is illustrated in FIGS. 1a to 4c. In U.S. Pat. No. 10,772,757, I proposed a tongue depressor portion 30 in which the mouthpiece bridge 26 defines one or more slots and the proximal end 32 of the tongue depressor portion 30 may include one or more flanges0 configured for insertion into respective slots, each of the slots and flanges having a plurality of flange openings and apertures adjacent one another and arranged in a longitudinal pattern, respective slot and flange combinations being in registration or alignment with one another.

Now, an embodiment of the present invention will be described with reference to FIGS. 1a to 2b and that includes a structure that is fast and easy for moving the tongue depressor portion 30 front-to-rear (longitudinally) and also upwardly-downwardly (e.g., vertically) relative to the mouthpiece portion 20 in ways that are simple, superior, and unique over all the other methods. More particularly, the proximal end 32 of the tongue depressor portion 30 may include a head member 35 that enables the proximal end 34 to be movably coupled to the bridge 26. More particularly, the head member 35 may have a generally planar or flat configuration that defines a slot 37. Then, the tongue depressor portion 30 includes a pair of adjustment fasteners particularly configured to enable forward/rearward movement and upward/downward movement of the tongue depressor portion 30, respectively.

First, the head member 35 may be coupled to the bridge 26 via a first fastener 39a such as a dental screw or the like that may be extended though the slot 37 and selectively rotated between loosened and tightened configurations. Accordingly, the head member 35 is slidably movable forwardly and rearwardly along the slot 37 and relative longitudinally to the mouthpiece portion 20 when the first fastener 39a is loosened from attachment to the bridge 26 (easing the compression between the head member 35 and the bridge 26) but is prevented from such movement when the first fastener 39a is tightened down (compressing the head member 35 against the bridge 26).

Figure 1B:
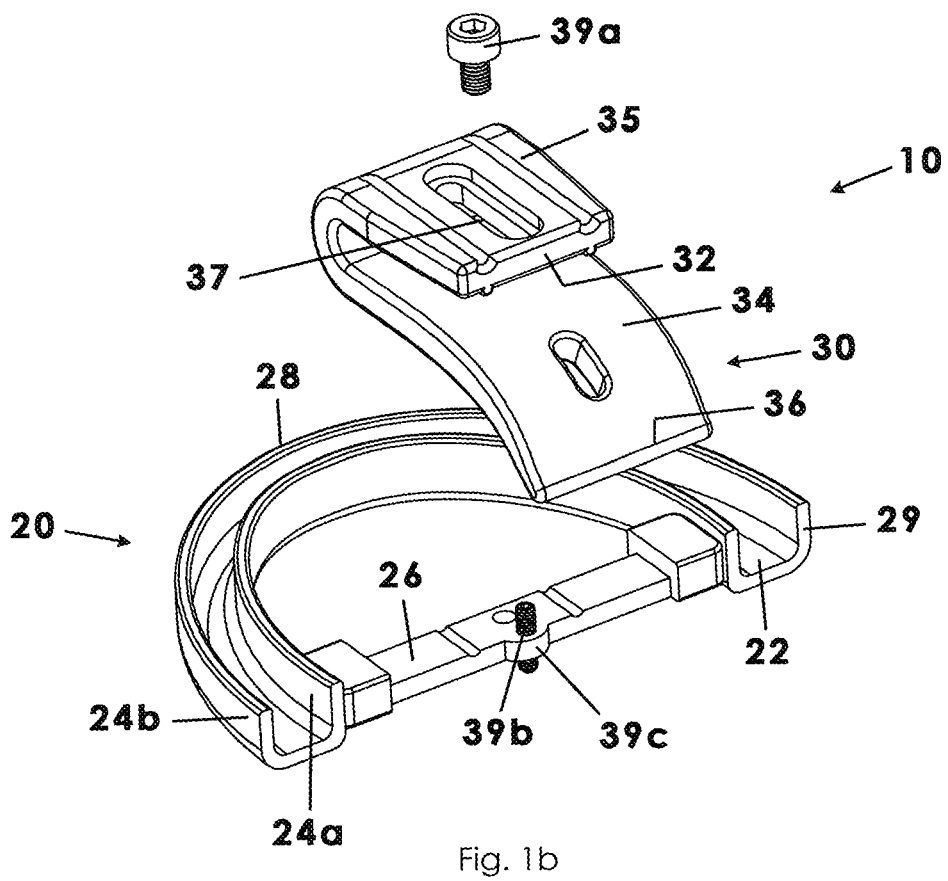
Figure 2A:
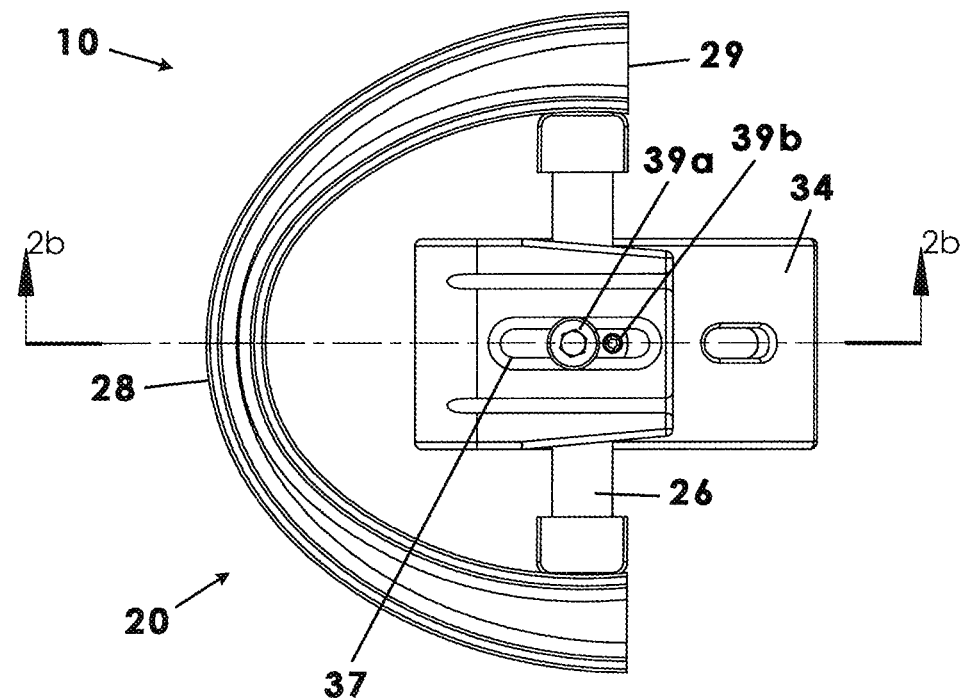
Figure 2B:
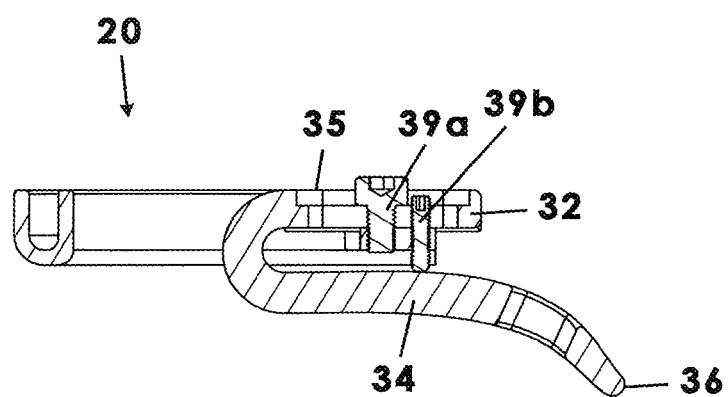

Second, a second fastener 39b is threadably coupled to the bridge 26 and is in operative contact with the body 34, whereby to cause the body 34 to flex upwardly or downwardly when the second fastener 39 is actuated (FIGS. 1a and 1b). More particularly, the second fastener 39b may be a set screw (i.e., a bolt that is fully threaded) threadably mounted in a mounting flange 39c associated with the bridge 26, the mounting flange 39c being internally threaded and operative so that the second fastener 39b rotates to move up or down, respectively. Preferably an end of the second fastener 39b bears against a surface of the body 34 and is operative to cause the body 34 to flex upwardly or downwardly relative to the mouthpiece portion 20 when the second fastener 39b is actuated.

It will be appreciated that both the first and second fasteners are "analog" in construction so as to allow almost infinite forward, rearward, upward, and downward adjustments, respectively. Specifically, each fastener may be incrementally rotated in direct relationship to linear movement of the head member 35 or body 34, respectively and, therefore, of the attached tongue depressor portion 30.

An embodiment of the anti-snoring mouthguard 10' according to another embodiment will be described with specific reference to FIGS. 3a to 4c. Primed reference characters will first be used with reference to structures that are substantially the same as those structures described above. First, the anti-snoring mouthguard 10' includes a mouthpiece portion 20' having a construction substantially similar to that first described herein. It is understood that primed reference characters associated with those already described above are used in the figures even though not recited a second time in the specification. In this embodiment, the bridge 26' includes a pair of bridge portions coupled together with fasteners such as with screws and is therefore vertically adjustable when said fasteners are alternatively loosened or tightened.

More particularly, the bridge 26' may include and upper portion 26a and a lower portion 26b that is coupled to a bottom side of the upper portion 26a with fasteners such as a pair of screws. Even more specifically, the upper portion 26a may include an elongate and linear configuration having a pair of opposed ends coupled to rear ends 29' of the mouthpiece portion 20', respectively, such as with screws or other equivalent fasteners (unnumbered). Similarly, the lower portion 26b may include an elongate and linear configuration having a pair of opposed ends, the lower portion 26b being coupled to a bottom side of the upper portion 26a with a pair of fasteners such as screws or the like (unnumbered). In an embodiment, the lower portion 26b may be movable between a loosened configuration displaced from the upper portion 26a and a tightened configuration sandwiched tightly against the upper portion 26a merely by adjusting or changing the rotational tightness of the respective screws. It can be seen that this is one means for adjusting the vertical placement of the body 34 although there is also another means for adjusting the vertical position thereof as will be described later.

In another aspect, the upper portion 26a of the bridge 26 defines a center slot 27a. Similarly, the lower portion 26b defines a center slot 27b. In a critical aspect, and adjustment fastener 21 is positioned longitudinally in the slot 27b (FIG. 3b) and is captured by lateral ends of the lower portion 26b of the bridge 26. The adjustment fastener 21 is fully threaded and rotatable although it is stopped by an end wall 23 at one end of the slot 27b; in other words, the adjustment fastener 21 does not itself move longitudinally although its actuation is functionally capable of adjusting the longitudinal position (i.e., frontward and back rearward movement of the tongue depressor portion 30' relative to the mouthpiece portion 20' as will be described further later.

Figure 3A:
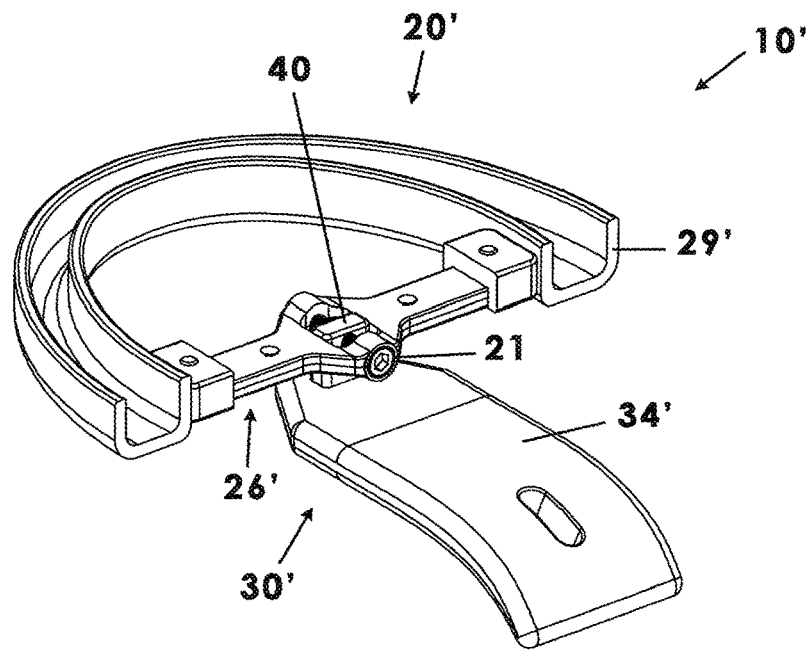
FIG. 3a is a perspective view of an anti-snoring mouth guard according to another embodiment of the present invention.
Figure 3B:
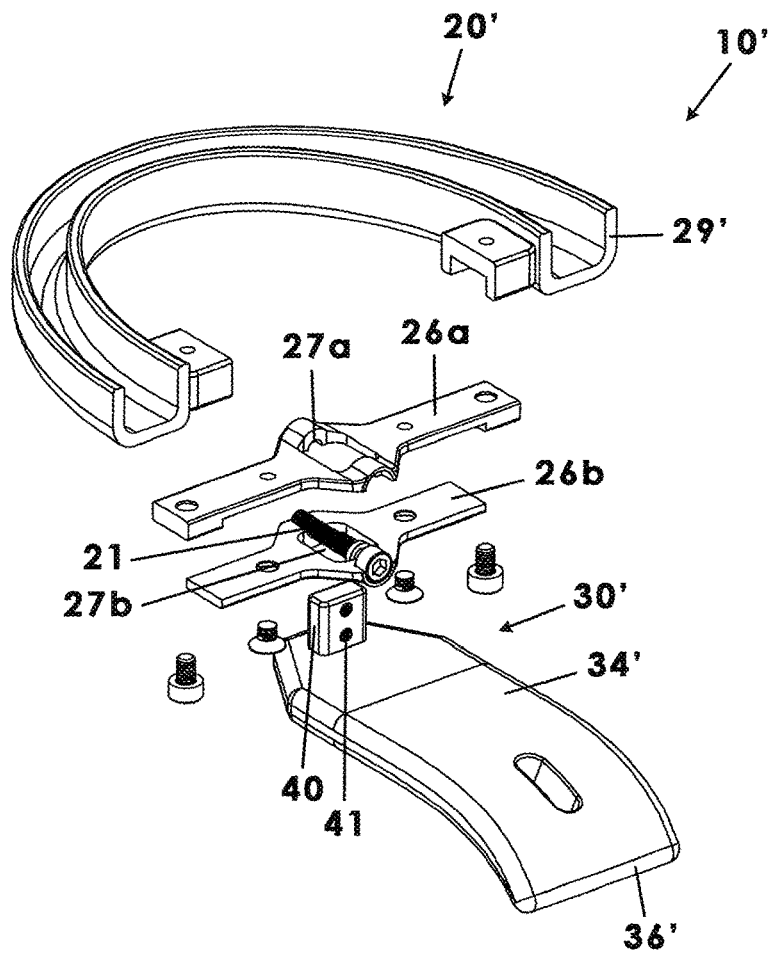
Figure 4A:
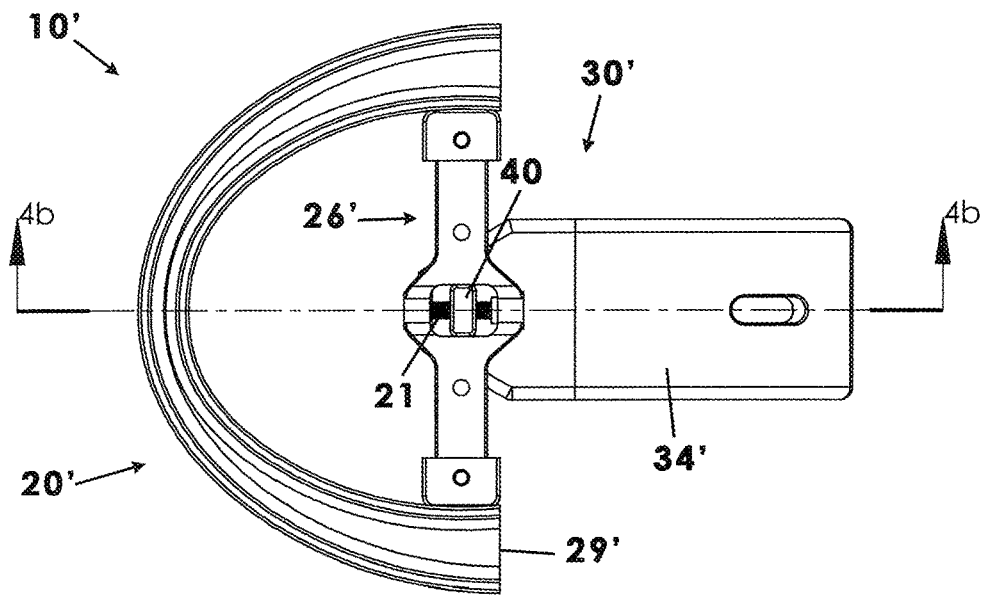
Figure 4B:
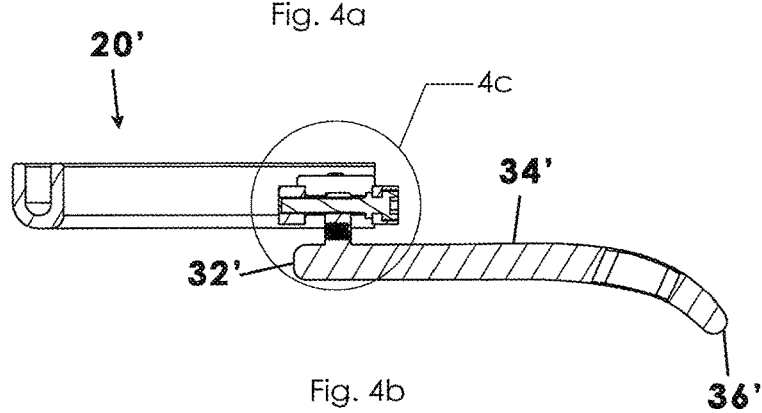
Figure 4C:
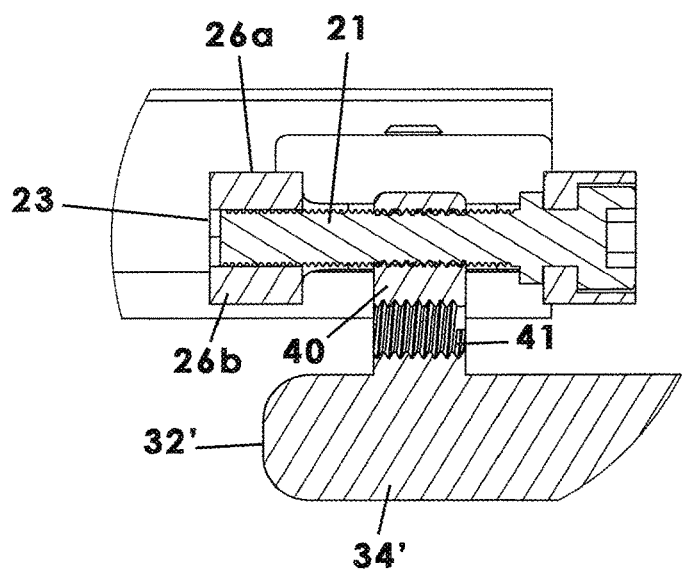
FIG. 4c is an isolated view on an enlarged scale taken from FIG. 4b.

In another aspect, the anti-snoring mouthguard according to this embodiment includes a tongue depressor portion 30' having a proximal end 32' and a body 34' coupled to the proximal end 32' that extends away from the mouthpiece portion 20' and at a downward angle. In a critical aspect that is unique to the anti-snoring mouthguard 10', a selection member 40 (also referred to simply as a selector) extends upwardly from the proximal end 32' of the body 34' and protrudes into the open space of the slot 27b (FIG. 3b). The selection member 40 may have a rectangular shape configuration that is perpendicular to the proximal end 32', the selection member 40 defining at least a pair of apertures which will be referred to as upper and lower apertures 41. It will be understood that the pair of apertures 41 may be aligned within the slot 27b such that the adjustment fastener 21 may be inserted through a selected one of the apertures 41, whereby to adjust the vertical position of the body 34'. In use, this vertical adjustment is likely performed by a dentist.

In use, it is understood that each aperture is threaded in a manner that is complementary to the thread pattern of the adjustment fastener 21. And, because the adjustment fastener 21 is captured, actuation of the adjustment fastener 21 causes the selection member 40 to move forwardly or rearwardly along the imaginary longitudinal axis defined by the adjustment fastener 21. Further, movement of the selection member 40 causes the body 34' to move forwardly or rearwardly in kind relative to the mouthpiece portion 20'. This structure, accordingly, is the forward and rear word adjustment of the tongue depressor portion 30' that is an object of the invention. Further, extending the adjustment fastener 21 through either the upper or lower aperture 41 member 40 is the vertical adjustment that is also an object of the invention.

Although a mouthpiece portion involving receiving only the upper teeth of a user's mouth is preferred, a mouthpiece portion designed to receive both upper and lower teeth is within the spirit of the present disclosure.

In use, a person may be fitted for a custom-built mouth guard by his or her dentist or technician. Preferably, the mouthpiece portion 20 is formed according to a scan or mold taken of the user's upper pallet of teeth. Then, the tongue depressor portion 30 may be adjusted according to the size and shape of the patient's tongue and mouth cavity, the elevation, forward, and rearward position being adjustable as described above.

Accordingly, a person simply inserts the mouth guard 10 into his mouth at bedtime and snoring is reduced. No longer is a CPAP machine needed as the mouth guard 10 prevents the user's tongue from rearward movement that closes the airway and causes snoring.

It is understood that while certain forms of this invention have been illustrated and described, it is not limited thereto except insofar as such limitations are included in the following claims and allowable functional equivalents thereof.

The invention claimed is:

1. An anti-snoring mouthguard, comprising:
a mouthpiece portion having a bottom wall and a pair of side walls opposite and parallel to one another and extending upwardly from the bottom wall so as to define a channel having a hemispherical configuration complementary to a shape of the user's teeth;
wherein said pair of side walls are continuous walls, respectively, and have a pair of rear ends that are terminal and that are open;
a bridge extending between said rear ends of said mouthpiece portion, said bridge including (1) an upper portion having a linear configuration and defining an upper slot and (2) a lower portion having a linear configuration and defining a lower slot that is coupled to a bottom side of said upper portion, said upper portion and said lower portion each having opposed ends coupled to said rear ends of said mouthpiece portion, respectively;
a tongue depressor portion having a proximal end, said tongue depressor portion having a body coupled to said proximal end and that extends away from said rear ends of said mouthpiece portion and at a downward angle;
a selector coupled to said proximal end and extending upwardly through said lower and upper slots, said selector defining upper and lower threaded apertures;
a fastener positioned longitudinally in said lower slot and extending threadably through a selected one of said upper and lower threaded apertures so as to determine a vertical distance between said tongue depressor portion and said mouthpiece portion,
said fastener being rotatably movable between a first rotational direction that causes said selector and said body to move in a rearwardly direction and a second rotational direction causing said selector and said body to move in a forwardly direction.

2. The anti-snoring mouthguard as in claim 1, wherein:
said fastener is a screw having a threaded configuration and a distal end that is captured and stopped from longitudinal movement between said upper and lower portions of said bridge; and
said selector is configured to travel forwardly and rearwardly along said fastener when said fastener is rotationally actuated.

* * * * *